(12) United States Patent
Beckers et al.

(10) Patent No.: US 12,031,925 B2
(45) Date of Patent: Jul. 9, 2024

(54) ADAPTABLE X-RAY ANALYSIS APPARATUS

(71) Applicant: Malvern Panalytical B.V., Almelo (NL)

(72) Inventors: Detlef Beckers, Almelo (NL); Alexander Kharchenko, Almelo (NL); Milen Gateshki, Almelo (NL)

(73) Assignee: Malvern Panalytical B.V., Almelo (NL)

( * ) Notice: Subject to any disclaimer, the term of this patent is extended or adjusted under 35 U.S.C. 154(b) by 0 days.

(21) Appl. No.: 17/899,096

(22) Filed: Aug. 30, 2022

(65) Prior Publication Data

US 2023/0270394 A1    Aug. 31, 2023

(30) Foreign Application Priority Data

Sep. 1, 2021    (EP) .................................. 21194395

(51) Int. Cl.
*G01N 23/20008* (2018.01)
*G01N 23/223* (2006.01)
(Continued)

(52) U.S. Cl.
CPC ..... *G01N 23/20008* (2013.01); *G01N 23/223* (2013.01); *A61B 6/40* (2013.01);
(Continued)

(58) Field of Classification Search
CPC ...... A61B 6/40; A61B 6/44; G01N 23/20008; G01N 23/223
See application file for complete search history.

(56) References Cited

U.S. PATENT DOCUMENTS 6,697,454 B1    2/2004 Nicolich et al.
2004/0062349 A1*   4/2004 Schuster ................ A61B 6/484
378/62
(Continued)

FOREIGN PATENT DOCUMENTS

EP    3294044 A1    3/2018
WO    2020229254 A1    11/2020

OTHER PUBLICATIONS

Modica et al., "X-Ray Production, Tubes and Generators", (Nov. 24, 2019), from the internet: <<http://web.archive.org/web/20191124054024/http://courses.washington.edu/radxphys/resources/resident_cheatsheets/X-Ray%20Prod%20Tubes%20Generators%20-%20Resident%20Cheat%20Sheet.pdf>> (Year: 2019).*
(Continued)

*Primary Examiner* — Chih-Cheng Kao
(74) *Attorney, Agent, or Firm* — LEASON ELLIS LLP

(57) ABSTRACT

The present invention relates to an X-ray analysis apparatus and a method of X-ray analysis. The X-ray analysis apparatus enables a user to carry out a plurality of X-ray analysis applications, for analysing a sample by measuring X-ray diffraction and/or X-ray fluorescence, using the same X-ray source. The apparatus comprises an X-ray source for irradiating the sample with X-rays, the X-ray source comprising a solid anode and a cathode for emitting an electron beam. It also comprises a focusing arrangement for focusing the electron beam onto the anode, and a controller. The controller is configured to receive X-ray analysis application information and to control the X-ray analysis apparatus to selectively operate in either a first X-ray analysis mode or a second X-ray analysis mode based on the X-ray analysis application information. In the first X-ray analysis mode the X-ray source operates at a first operating power and has an effective focal spot size that is less than 100 μm. In the second X-ray analysis mode the X-ray source operates at a
(Continued)

second operating power that is higher than the first operating power, and the area of the effective focal spot is larger than the area of the effective focal spot in the first X-ray analysis mode.

15 Claims, 6 Drawing Sheets

(51) Int. Cl.
*H05G 1/52* (2006.01)
*A61B 6/00* (2024.01)
*A61B 6/40* (2024.01)
*A61B 6/42* (2024.01)

(52) U.S. Cl.
CPC ............... *A61B 6/4208* (2013.01); *A61B 6/44* (2013.01); *H05G 1/52* (2013.01)

(56) References Cited

U.S. PATENT DOCUMENTS

| | | | | |
|---|---|---|---|---|
| 2004/0228439 | A1* | 11/2004 | Tsujii | A61B 6/06 378/62 |
| 2006/0133575 | A1* | 6/2006 | Gutman | A61N 5/1001 378/65 |
| 2007/0183560 | A1* | 8/2007 | Popescu | A61B 6/482 378/5 |
| 2013/0108015 | A1* | 5/2013 | Kottler | G21K 1/067 378/36 |
| 2014/0219424 | A1 | 8/2014 | Smith et al. | |
| 2019/0159742 | A1* | 5/2019 | Behling | A61B 6/502 |
| 2020/0098537 | A1 | 3/2020 | Yun et al. | |

OTHER PUBLICATIONS

European Search Report in EP Application No. 21194395.6-1001, mailed Mar. 7, 2022 (7 pages).
Communication pursuant to Article 94(3) EPC in EP Application No. 21194395.6, mailed Mar. 22, 2024. 4 pages.

* cited by examiner

ADAPTABLE X-RAY ANALYSIS APPARATUS

CROSS-REFERENCE TO RELATED PATENT APPLICATIONS

This application claims the priority from European Application No. 21194395.6, filed Sep. 1, 2021, which is incorporated by reference, as if expressly set forth in its respective entireties herein.

FIELD OF THE INVENTION

The present invention relates to an apparatus and method for X-ray analysis. Embodiments relate, in particular, to an X-ray analysis apparatus for carrying out multiple X-ray analysis applications. More particularly, embodiments relate to an X-ray analysis apparatus for carrying out analysis of a sample by X-ray diffraction, X-ray scattering or X-ray fluorescence.

BACKGROUND

Typically, X-ray generating devices (e.g. X-ray tubes) comprise a cathode and an anode. The cathode is arranged to irradiate a surface of the anode with an electron beam, and X-rays are emitted from the irradiated area. The irradiated area of the anode is known as the focal spot.

Some X-ray tubes have rotating anodes, in which the anode rotates during operation. Some other X-ray tubes have fixed anodes, which remain stationary during operation.

In general, an X-ray tube comprises a housing that encloses the cathode and the anode. In some arrangements, the surface of the anode irradiated by the electron beam is inclined at an oblique angle with respect to the electron beam. In these arrangements, the size of the focal spot as viewed from a measuring device measuring the X-ray beam emitted from the X-ray tube (known as the "effective focal spot") is different to the size of the irradiated area of the anode. The size of the effective focal spot can be measured according to European Standard EN 12543: 1999 (parts 1 to 5).

For conventional solid-anode X-ray tubes, the surface temperature of the anode during operation should be much lower (e.g. 100 degrees centigrade lower) than the melting point of the anode in order to avoid damage to the anode. For this reason, there may be a trade-off between the area of the effective focal spot and the optimum operating power setting. For example, in some applications it is desired to use a focal spot with a small area. To accommodate this, whilst avoiding damage to the anode, the maximum power appropriate for the small-focus X-ray tube compared to X-ray tubes with larger focal spots is relatively low.

The optimum operating power setting of an X-ray tube—which is a combination of the voltage drop between the anode and the cathode (the operating voltage, kV) and an emission current (mA) i.e. the flow of electrons from the cathode to the anode—is typically determined as part of the manufacturing process. The optimum operating power setting takes into account various factors that can affect the behaviour of the electron beam. One such factor is the internal geometry of the X-ray tube surrounding the anode and the cathode. For that reason, each individual X-ray tube typically has an associated operating power, which is determined during manufacture (e.g. the X-ray tube may be a "50 W X-ray tube"). This allows the user to operate the X-ray tube in a way that that will ensure the X-ray tube functions correctly, whilst also ensuring reliability and longevity.

Users typically select an X-ray tube for an X-ray analysis apparatus based on the specific X-ray analysis application to be carried out. In this way, the user can select an X-ray tube appropriate for the relevant X-ray analysis application. Some X-ray analysis applications, such as powder diffraction on a large sample, can be carried out using an X-ray beam having a large focal spot, enabling relatively high intensity measurements. However, some other X-ray analysis applications require the use of a small-focus X-ray tube (e.g. X-ray tubes having an effective focal spot size of less than 300 µm). The small focal spot means the tube is operated at a relatively low operating power, resulting in relatively low intensity measurements. For example, X-ray diffraction applications such as two-dimensional small angle X-ray scattering (2D SAXS), grazing incidence small angle X-ray scattering (GISAXS) and micro-diffraction measurements are all typically carried out using micro-focus X-ray tubes (X-ray tubes having an effective focal spot size of less than 100 µm). Alternatively, these applications can be carried out using an X-ray tube having a larger effective focal spot, in combination with collimating optics that reduce the size of the X-ray beam before it irradiates the sample, which significantly reduces intensity.

Small-focus X-ray tubes are typically directly coupled (i.e. fixed) to the optics required for the particular X-ray analysis application.

It would be desirable to be able to use an X-ray analysis apparatus to carry out multiple different types of X-ray analysis applications, whilst minimising the need for reconfiguration of the X-ray analysis apparatus.

SUMMARY

According to an aspect of the invention, there is provided an X-ray analysis apparatus for carrying out a plurality of X-ray analysis applications to analyse a sample by measuring X-ray diffraction and/or X-ray fluorescence, the apparatus comprising:
  an X-ray source for irradiating the sample with X-rays, the X-ray source comprising:
    a solid anode; and
    a cathode for emitting an electron beam;
  a focusing arrangement for focusing the electron beam onto the anode; and
  a controller configured to receive X-ray analysis application information and to control the X-ray analysis apparatus to selectively operate in either a first X-ray analysis mode or a second X-ray analysis mode based on the X-ray analysis application information, wherein:
  in the first X-ray analysis mode the X-ray source is controlled to operate at a first operating power, at a first operating voltage, and has an effective focal spot size that is less than 100 µm; and
  in the second X-ray analysis mode the X-ray source is controlled to operate at a second operating power, at a second operating voltage, wherein the second operating power is greater than the first operating power, and the area of the effective focal spot is greater than the area of the effective focal spot in the first X-ray analysis mode.

The controller is configured to control the X-ray analysis apparatus to operate in either the first X-ray analysis mode or the second X-ray analysis mode. The controller may comprise an input for receiving information relating to the X-ray analysis application. The X-ray analysis application may be an X-ray diffraction application, an X-ray fluorescence application, or an application that combines both X-ray diffraction analysis and X-ray fluorescence analysis.

The operating voltage refers to the high voltage applied across the anode and the cathode to cause electrons to move from the cathode to the anode. The first operating voltage may be equal to or different to the second operating voltage. In some embodiments, the first operating voltage is 60 kV and the second operating voltage is 60 kV. In some embodiments, the effective focal spot size of the first X-ray analysis mode is smaller than the effective focal spot size of the second X-ray analysis mode. The X-ray analysis application information is information relating to the type of X-ray analysis application to be carried out. It may be information relating to an incident-beam X-ray optic used in the X-ray analysis application. For example, the controller may be configured to operate the X-ray analysis apparatus in the first or second X-ray analysis mode based on the information identifying the X-ray optic, or may be configured to operate the X-ray analysis apparatus in the first or second X-ray analysis mode based on other information relating to the X-ray optic (e.g. whether or not the X-ray optic is arranged to receive the X-ray beam).

In some embodiments, the X-ray analysis application information may comprise information identifying the X-ray analysis application. In some embodiments, the X-ray analysis application information may comprise information about the sample e.g. the size of the sample.

The effective focal spot size is determined by the length (l) or the width (w) of the effective focal spot, depending on which is largest. The area of the effective focal spot is the product of the measured length and measured width. For a substantially circular focal spot, the diameter measured to determine the length and width.

The anode may be a fixed anode. That is, the anode remains stationary during operation, as opposed to a rotating anode, which rotates about its axis during operation.

The effective focal spot is the focal spot as observed at the X-ray beam which may or may not have equal dimensions to the irradiated area of the anode.

In some embodiments, in the first X-ray analysis mode the X-ray source has an effective focal spot size less than 55 µm and in the second X-ray analysis mode the effective focal spot size is greater than 60 µm.

In some embodiments, the effective focal spot may be substantially circular (or square) in the first X-ray analysis mode. In those embodiments, the diameter (or length) of the effective focal spot is less than 55 µm. In the second X-ray analysis mode, the effective focal spot may be "line-shaped"—that is, it may be rectangular—or elliptical, and one of the width and the length of the effective focal spot may be greater than 60 µm, so long as the area of the effective focal spot in the second X-ray analysis mode is greater than the area of the effective focal spot in the first X-ray analysis mode. Alternatively, both the width and the length of the effective focal spot may be greater than 60 µm in the second X-ray analysis mode.

The X-ray analysis apparatus may further comprise a first interchangeable X-ray optic arranged to receive X-rays from the X-ray source.

The first interchangeable X-ray optic may be arranged between the X-ray source and the sample. In this regard, the X-ray optic is not fixed to the X-ray source and is accordingly interchangeable.

The controller may be configured to receive information identifying the first interchangeable X-ray optic, and wherein the controller is configured to operate the X-ray analysis apparatus in either the first X-ray analysis mode or the second X-ray analysis mode based on the information identifying the first interchangeable X-ray optic.

The X-ray analysis application information may be the name of the X-ray analysis application, which may have a one-to-one correspondence with the X-ray optic to be used for the X-ray analysis application. In this way, the name of the X-ray analysis application may identify the X-ray optic. The interchangeable optic may be configured to be exchanged manually. The X-ray analysis apparatus may further comprise a second interchangeable X-ray optic, and the controller may be configured to operate the X-ray analysis apparatus in either the first X-ray analysis mode or the second X-ray analysis mode based on the information identifying the second interchangeable X-ray optic.

In some embodiments, the effective focal spot may have an aspect ratio greater than 2.0 in both the first X-ray analysis mode and the second X-ray analysis mode, and the controller may be configured to receive sample information and to operate the X-ray analysis apparatus in the first X-ray analysis mode or the second X-ray analysis mode based on the sample information.

The sample information may relate to the dimensions of the sample, or the type of sample to be analysed, or the type of analysis to be carried out on the sample. The aspect ratio is the ratio of the effective focal spot size to the other of length and width. For example, if the effective focal spot size is determined by the length of the focal spot, the aspect ratio is the ratio of length to width.

In some embodiments, in the first X-ray analysis mode, the effective focal spot size may be less than 40 µm, the aspect ratio of the effective focal spot may be less than 1.5 and the first operating power may be less than 50 W.

Optionally, the size of the effective focal spot may be less than 25 µm. This X-ray analysis mode may be suitable for use with multi-layer two-dimensional mirrors, which are used in X-ray analysis applications such as 2D Small Angle X-ray Scattering (2D SAXS), Grazing Incidence Small Angle X-ray Scattering (GISAXS), Micro-diffraction and Computed Tomography.

In some embodiments, in the second X-ray analysis mode, the effective focal spot size may be greater than in the first X-ray analysis mode and greater than 60 µm, the aspect ratio of the effective focal spot may be less than 1.5, and the second operating power may be greater than 50 W.

This mode may be particularly suitable for use with mono-capillary or poly-capillary collimators, which can be used in X-ray analysis applications such as stress and texture measurements.

In some embodiments, in the first X-ray analysis mode, the effective focal spot may have an aspect ratio that is less than 1.5, and in the second X-ray analysis mode the focal spot may be elongate and may have an aspect ratio that is greater than 2.0.

In some embodiments, in the second X-ray analysis mode the effective focal spot size may be greater than 60 µm and the second operating power may be greater than 50 W. This mode may be particularly suitable for use with a collimating slit, a one-dimensional mirror or a hybrid monochromator.

In some embodiments, the effective focal spot size in the second X-ray analysis mode may be greater than 100 µm, and the second operating power may be equal to or greater than 100 W. Accordingly, in the second X-ray analysis mode, the X-ray source can operate at an operating power that is significantly larger than is typical for X-ray tubes capable of forming a micro-focus.

In some embodiments, the X-ray analysis apparatus may further comprise:

a sample stage for supporting the sample, wherein the sample stage is arranged such that the X-ray source irradiates the sample with X-rays directed along an incident beam path; and a detector arranged to receive X-rays scattered by the sample or emitted from the sample.

The X-ray analysis apparatus is accordingly configured for XRF analysis, X-ray scattering analysis, XRD analysis, Computed Tomography or X-ray imaging.

The X-ray analysis apparatus may comprise a first interchangeable X-ray optic, and the X-ray analysis apparatus may further comprise:

a first actuator configured to move the first interchangeable X-ray optic between an in-beam position, in which the first interchangeable X-ray optic is arranged in the incident beam path, and an out-of-beam position, in which the first interchangeable X-ray optic is arranged outside of the incident beam path;

wherein the controller is configured to receive information identifying the position of the first interchangeable X-ray optic and to operate the X-ray analysis apparatus in the first X-ray analysis mode or the second X-ray analysis mode based on the position of the first interchangeable X-ray optic.

The X-ray analysis apparatus may further comprise a second interchangeable X-ray optic, which is different to the first interchangeable X-ray optic. The X-ray analysis apparatus may be configured to move the second interchangeable X-ray optic between an in-beam position, in which the second interchangeable X-ray optic is arranged in the incident beam path, and an out-of-beam position, in which the second interchangeable X-ray optic is arranged outside of the incident beam path. The controller may be configured to receive information identifying the position of the second X-ray optic and to operate the X-ray analysis apparatus in the first X-ray analysis mode or the second X-ray analysis mode based on the position of the second interchangeable X-ray optic. The information may be input by a user, or sent to the controller by a sensor configured to determine whether at least one of the optics is in an in-beam position. The controller may be configured to operate the X-ray analysis apparatus in the first X-ray analysis mode when the first interchangeable X-ray optic is in its in-beam position and the second interchangeable X-ray optic is in its out-of-beam position, and to operate the X-ray analysis apparatus in the second X-ray analysis mode when the second interchangeable X-ray optic is in its in-beam position and the first interchangeable X-ray optic is in its out-of-beam position.

According to an aspect of the invention, there is provided a method of controlling the X-ray analysis apparatus, as described above, comprising:

receiving, by a controller, X-ray analysis application information;

selecting a first X-ray analysis mode or a second X-ray analysis mode based on the X-ray analysis application information; and controlling the X-ray source to operate in the selected mode, wherein:

in the first X-ray analysis mode the X-ray source is controlled to operate at a first operating power, and has an effective focal spot size that is less than 100 µm; and in the second X-ray analysis mode the X-ray source is controlled to operate at a second operating power, which is higher than the first operating power, and the area of the effective focal spot is greater than the area of the effective focal spot in the first X-ray analysis mode.

The information identifying the X-ray analysis application may comprise information identifying a first interchangeable X-ray optic or information identifying the position of a first interchangeable X-ray optic and/or a second interchangeable X-ray optic.

In some embodiments, in the first X-ray analysis mode the X-ray source may have an effective focal spot size less than 55 µm and in the second X-ray analysis mode the effective focal spot size may be greater than 60 µm.

The method may comprise receiving information identifying the first interchangeable X-ray optic, and controlling the X-ray analysis apparatus to operate in the first X-ray analysis mode or the second X-ray analysis mode based on the information identifying the first interchangeable X-ray optic.

The effective focal spot may have an aspect ratio greater than 2.0 in both the first X-ray analysis mode and the second X-ray analysis mode, and the method may comprise receiving sample information and controlling the X-ray analysis apparatus to operate in the first X-ray analysis mode or the second X-ray analysis mode based on the sample information.

In the first X-ray analysis mode the effective focal spot size may be less than 40 µm, the aspect ratio of the effective focal spot may be less than 1.5 and the first operating power may be less than 50 W.

In the second X-ray analysis mode, the effective focal spot size may be greater than in the first X-ray analysis mode and greater than 60 µm, the aspect ratio of the effective focal spot may be less than 1.5, and the second operating power may be greater than 50 W.

In the first X-ray analysis mode, the effective focal spot may have an aspect ratio that is less than 1.5, and in the second X-ray analysis mode the focal spot may be elongate and may have an aspect ratio that is greater than 2.0.

In the second X-ray analysis mode the effective focal spot size may be greater than 60 µm and the second operating power may be greater than 50 W.

The effective focal spot size in the second X-ray analysis mode may be greater than 100 µm, and the second operating power may be equal to or greater than 100 W.

The X-ray source may irradiate the sample with X-rays directed along an incident beam path; and a detector may receive X-rays scattered by the sample or emitted from the sample.

The controller may receive information identifying the position of a first interchangeable X-ray optic and may control the X-ray analysis apparatus to operate in the first X-ray analysis mode or the second X-ray analysis mode based on the position of the first interchangeable X-ray optic.

According to an aspect of the invention, there is provided a computer program product comprising a tangible non-transitory computer readable medium in which program instructions are stored, wherein the program instructions cause the above-described X-ray analysis apparatus to execute the steps of the above-described method.

The program instructions may cause the X-ray analysis apparatus described above to execute any of the methods described above.

BRIEF DESCRIPTION OF THE DRAWINGS

Embodiments of the present invention will now be described, by way of example, with reference to the accompanying drawings, in which.

Figure 1:
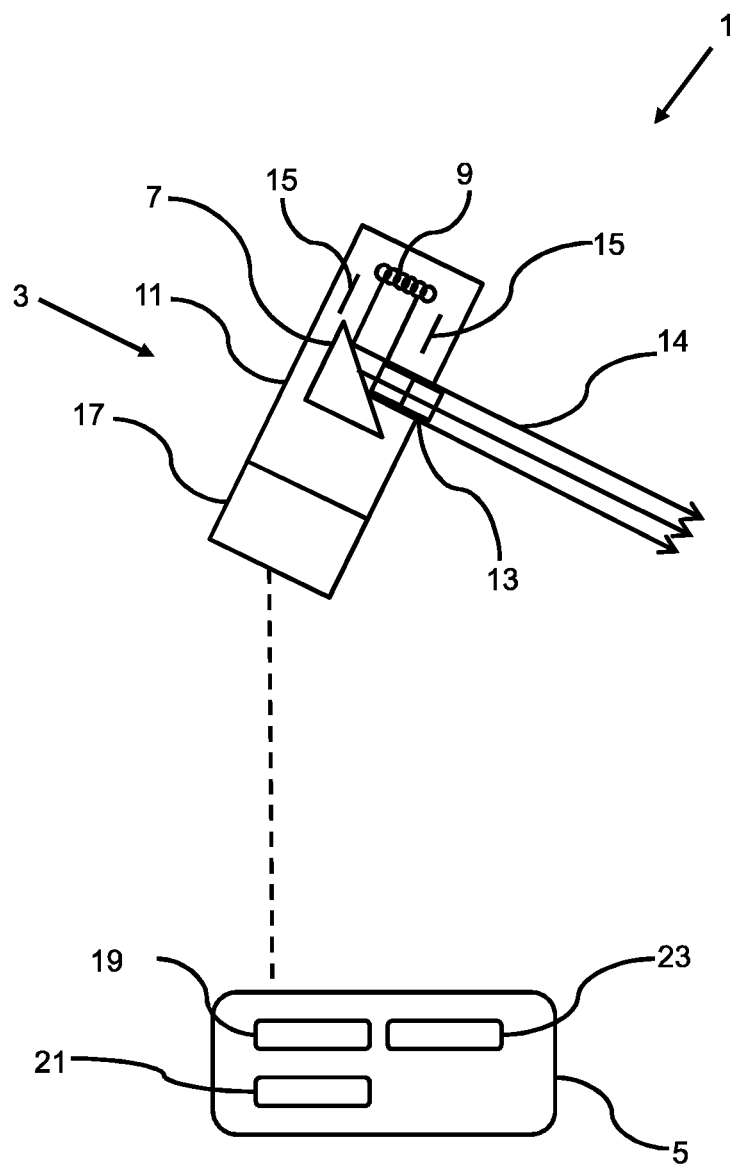
FIG. 1 is a schematic diagram illustrating an X-ray analysis apparatus according to an embodiment of the invention.

It should be noted that these figures are diagrammatic and not drawn to scale. Relative dimensions and proportions of parts of these figures have been shown exaggerated or reduced in size, for the sake of clarity and convenience in the drawings.

DETAILED DESCRIPTION

FIG. 1 shows an X-ray analysis apparatus 1 including an X-ray source 3 and a controller 5. It will be appreciated that, whilst not shown in FIG. 1, the X-ray analysis apparatus 1 may also include a sample stage, for supporting a sample to be analysed, and an X-ray detector.

Referring to FIG. 1, the X-ray source 3 (which is an X-ray tube) includes a solid anode 7 and a cathode 9 enclosed in a sealed housing 11. The housing 11 includes a window 13 arranged to allow X-rays 14 from the anode 7 to exit the housing. The anode 7 is a fixed anode, as opposed to a rotating anode. That is, the anode 7 is fixed in position and remains stationary with respect to the housing 11. As previously mentioned the anode 7 is solid, rather than a liquid-type anode (for comparison, some X-ray sources include liquid-type anodes which are designed so that the cathode irradiates a liquid jet of material during operation).

In some embodiments, the cathode 9 is a wound tungsten filament and the anode 7 comprises copper. However, either or both of the anode 7 and the cathode 9 may comprise alternative materials. For example, the anode 7 may comprise copper, chromium, cobalt molybdenum, silver, gold, rhodium, iron or tungsten.

In the embodiment illustrated in FIG. 1, a focusing arrangement 15 is located inside the housing 11, between the anode 7 and the cathode 9. The focusing arrangement 15 is configured to influence the electric field inside the housing 11, so as to guide electrons emitted by the cathode 9 towards the anode 7 and, moreover, to influence the shape and/or size of the area of the anode 7 irradiated by the electrons. For example, and as schematically depicted in FIG. 1, the focusing arrangement may comprise a plurality of metal grids. However, the skilled person will understand that a single metal grid may alternatively be used, or an alternative focusing device could be used. For example, the focusing arrangement may be a magnetic focusing arrangement that uses magnetic fields to focus the X-rays e.g. a quadrupole field. The voltage supplied to the grids may be varied in order to adjust the electric field inside the X-ray tube, and in particular in the vicinity of the electron beam irradiating the anode 7.

The X-ray source 3 further comprises control electronics 17, for adjusting various operating parameters including the operating voltage of the X-ray tube, the emission current of the X-ray tube (by adjusting the current supplied to the cathode and/or the operating voltage) and control parameters of the focusing arrangement 15 such as the voltage applied to the focusing arrangement 15.

In embodiments, the X-ray analysis apparatus is controlled to operate in at least two modes. In the first X-ray analysis mode, the effective focal spot size is less than 100 µm. Accordingly, the X-ray source can be used for X-ray analysis applications requiring a micro-focus source. In the second X-ray analysis mode, the operating power of the X-ray tube is increased. Additionally, the irradiated area of the anode is increased (and accordingly the area of the focal spot as viewed from a measuring device measuring the X-ray beam emitted from the X-ray tube—i.e. the area of the effective focal spot—is also increased). In this way, the X-ray tube can be used for a variety of X-ray analysis applications, in a convenient way, whilst mitigating the risk of damage to the X-ray tube (and in particular to the anode). For X-ray analysis applications requiring a very small focal spot, the X-ray analysis apparatus is operated in the first X-ray analysis mode at an appropriate operating power setting. In addition, if a larger focal spot is required for a different X-ray analysis application, the X-ray analysis apparatus is operated in the second X-ray analysis mode. In other words, X-ray analysis apparatus may be operated in a first mode that focuses the beam to a small spot on the anode, or in a second mode that de-focuses the beam to a larger spot on the anode.

In addition to the X-ray source 3, the X-ray analysis apparatus 1 comprises a controller 5 in communication with the control electronics 17. The controller 5 comprises a memory 19 for storing X-ray analysis mode information, an input 21 for receiving X-ray analysis application information, and a processor 23 for selecting the X-ray analysis mode of the X-ray tube in response to the received X-ray analysis application information. The X-ray analysis mode information comprises operating parameter values for at least two X-ray analysis modes. The controller 5 is configured to cause the control electronics 17 of the X-ray tube to operate the X-ray tube according to the X-ray analysis mode selected by the controller 5.

In some embodiments, the aspect ratio of the effective focal spot is less than 1.5 in both the first X-ray analysis mode and the second X-ray analysis mode. For example, in the first X-ray analysis mode the focal spot may be substantially circular and the effective focal spot may have a diameter of 20 µm and the operating power of the X-ray tube may be 50 W or less. In the second X-ray analysis mode, the diameter of the effective focal spot may be 40 µm. The area of the effective focal spot in the second X-ray analysis mode is accordingly significantly higher than in the first X-ray analysis mode. It is therefore possible to increase the operating power in the second X-ray analysis mode, without causing damage to the X-ray tube. In this way, the X-ray analysis application facilitates the use of differently sized focal spots, with an operating power tailored to the size of the spot.

Similarly, the effective focal spot could be elongate. In the first X-ray analysis mode, the effective focal spot may have a maximum dimension (length/width) of 20 µm and the operating power of the X-ray tube may be 50 W or less. In the second X-ray analysis mode, the maximum dimension (length/width) of the effective focal spot may be 40 µm. The area of the effective focal spot in the second X-ray analysis mode may be significantly higher than in the first X-ray analysis mode. It is therefore possible to increase the operating power in the second X-ray analysis mode, without causing damage to the X-ray tube. In this way, the X-ray analysis application facilitates the use of differently sized focal spots, with an operating power tailored to the size of the spot.

In some embodiments, the first X-ray analysis mode may have an effective focal spot with an aspect ratio (the ratio of the larger of length/width to the other of length/width) that is close to 1 (i.e. between 1 and 1.5). However, in the second X-ray analysis mode, the effective focal spot may be elongate. That is, the effective focal spot may have an aspect ratio that is equal to or greater than 2.0. In this way, the X-ray analysis apparatus can be used both for X-ray analysis applications that require a line-shaped focus as well as X-ray analysis applications for which a line-shaped focus is not desired/appropriate.

In some embodiments, both the first X-ray analysis mode and the second X-ray analysis mode have an elongate effective focal spot. The aspect ratio of the effective focal spot may be larger in the second X-ray analysis mode than in the first X-ray analysis mode.

The inventors have realised that by providing an X-ray source including a solid, fixed anode together with a focusing arrangement configured to influence an electron beam from a cathode and a controller configured to control the focusing arrangement according to a selected X-ray analysis mode, the X-ray source is long lasting, economical and convenient-to-use. In particular, the X-ray source can be controlled to operate in multiple different X-ray analysis modes, according to the X-ray analysis to be carried out. In the first X-ray analysis mode, the effective focal spot size is less than 100 μm (i.e. the length or width, or diameter, is less than 100 μm). Accordingly, in the first X-ray analysis mode, the X-ray tube has a micro-focus, and the operating power is relatively low (as compared to the second X-ray mode) to protect the anode. In the second X-ray analysis mode, both the operating power of the X-ray tube and the irradiated area of the anode are increased. In this way, the X-ray tube can be used with a variety of X-ray analysis applications, in a convenient way, with minimal damage to the anode.

Operating parameters for two illustrative examples of X-ray analysis modes, together with the respective effective focal spot dimensions, are described below in Table 1. The operating voltage is the high voltage applied across the anode.

TABLE 1

Example X-ray analysis modes

| X-ray analysis mode | Operating voltage (kV) | Filament current (mA) | Focusing arrangement voltage | Effective focal spot dimensions (μm$^2$) |
|---|---|---|---|---|
| Mode 1 | 45 | 1.0 | low | 50 × 50 |
| Mode 2 | 50 | 1.8 | high | 60 × 160 |

As shown in FIG. 1, the controller 5 comprises an input 21, which is an interface for receiving X-ray analysis application information. The input 21 enables a user to enter X-ray analysis application information such as identification of the X-ray analysis to be conducted, the type of sample to be analysed, and/or the size of the sample to be analysed, or information relating to the X-ray analysis apparatus (e.g. by specifying an optic to be used during the X-ray analysis).

The processor 23 is configured to determine which X-ray analysis mode the X-ray tube should operate in based on the received X-ray analysis application information. Once the X-ray analysis mode has been selected, the controller 5 causes the X-ray source 3 to operate in the selected mode. The input 21 may be configured to receive alphanumeric data. The input 21 may be configured to receive data via a user input device (e.g. a keyboard), by a wired connection and/or it may comprise a receiver for receiving data by a wireless connection.

The X-ray analysis to be conducted may refer to a particular type of measurement technique e.g. 2D Small Angle X-ray Scattering (2D SAXS), Grazing Incidence Small Angle X-ray Scattering (GISAXS), Micro-diffraction, Computed Tomography, Residual stress analysis, Texture analysis, Bragg Brentano analysis, or any other type of X-ray analysis technique.

In some embodiments, the X-ray analysis apparatus 1 may comprise an interchangeable optic, and the controller 5 may be configured to select the X-ray analysis mode based on the interchangeable optic. An example of such an embodiment is described in connection with FIG. 2.

Figure 2:
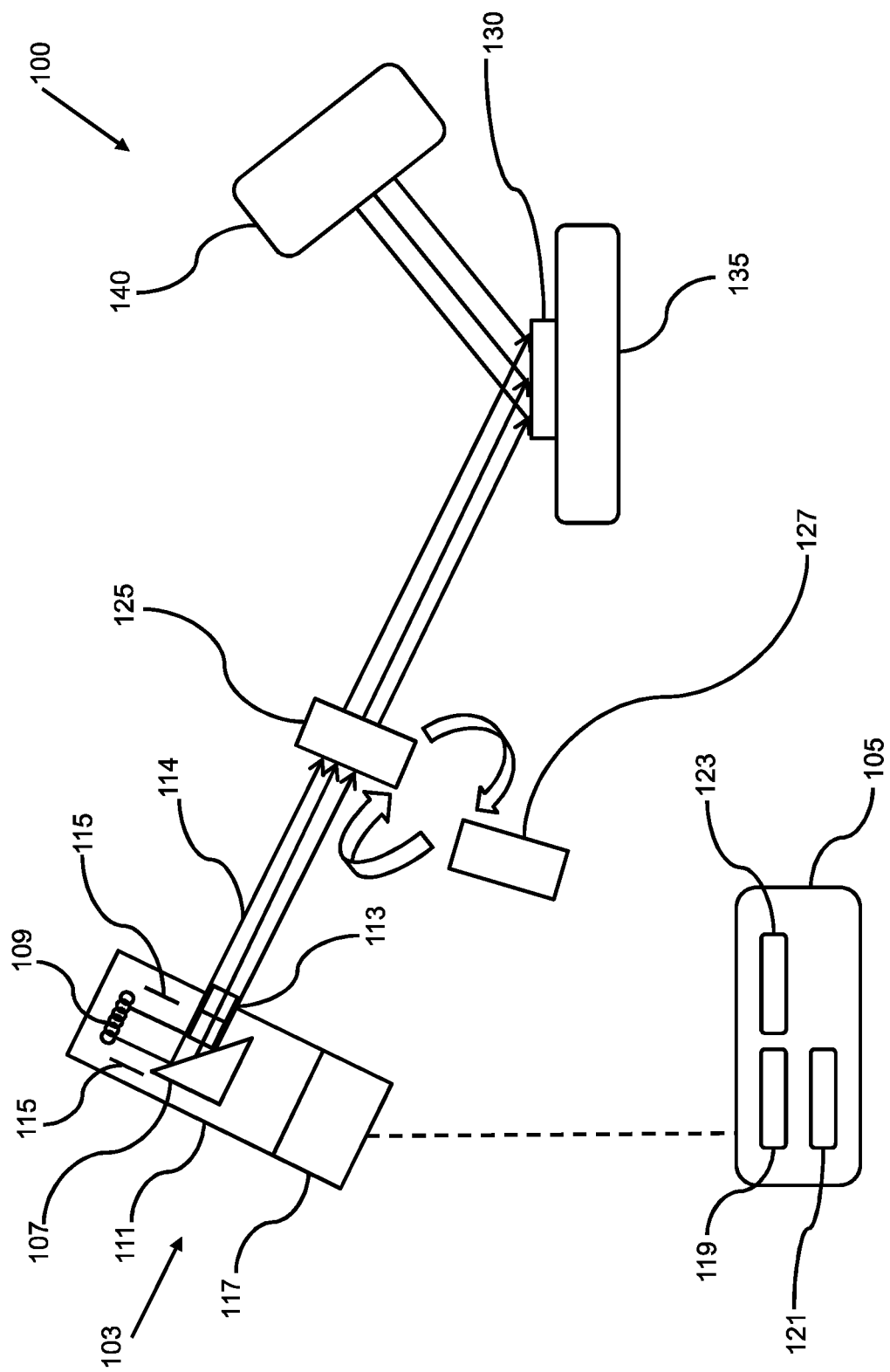
FIG. 2 is a schematic diagram illustrating an X-ray analysis apparatus according to another embodiment of the invention.

FIG. 2 shows an X-ray analysis apparatus 100, in which the X-ray analysis apparatus 100 comprises a first interchangeable optic 125.

The X-ray analysis apparatus 100 is similar to the X-ray analysis apparatus in FIG. 1, and additionally includes a sample stage 135 supporting a sample 130 to be analysed. It also includes an X-ray detector 140 arranged to receive X-rays scattered (e.g. diffracted) by the sample 130. In some embodiments, the X-ray detector 140 may be an X-ray fluorescence detector, and may be positioned differently than is shown in FIG. 2.

The X-ray source 103, which is an X-ray tube, comprises an anode 107 and a cathode 109 inside a sealed housing 111. A focusing arrangement 115 is also arranged inside the housing 111, between the anode 107 and the cathode 109. The X-ray source comprises control electronics 117, for controlling various operating parameters including the cathode current, the voltage drop across the cathode and anode, and the voltage applied to the focusing arrangement 115. X-rays 114 from the anode 107 exit the housing 111 via a window 113. In FIG. 2, the first interchangeable optic 125 is positioned in the path of the X-rays 114 from the X-ray tube. Accordingly, the first interchangeable optic 125 receives X-rays directly from the X-ray tube. The X-rays pass through the first interchangeable optic 125 before irradiating the sample 130. X-rays from the sample are received by the X-ray detector 140.

The first interchangeable optic 125 is not fixed to the housing 111. It can be removed from the X-ray analysis apparatus and replaced with a different optic. In some embodiments, the interchangeable optic is replaced manually by an operator. Alternatively, the X-ray analysis apparatus may comprise at least one actuator for removing and/or replacing the first interchangeable optic 125. In some embodiments, the interchangeable optic is arranged to receive X-rays directly from the X-ray source. That is, the X-rays from the source do not pass through an intervening optic before reaching the first interchangeable optic 125.

The first interchangeable optic 125 is selected based on the X-ray analysis application to be carried out. For example, the first interchangeable optic 125 may comprise a two-dimensional focusing mirror, which is typically used for two dimensional (2D) Small Angle X-ray Scattering (2D SAXS), Grazing Incidence Small Angle X-ray Scattering (GISAXS) or Micro-diffraction. In some other embodiments, the first interchangeable optic 125 may be a monocapillary collimator or a polycapillary collimator; these optics can be used to carry out stress analysis by XRD or texture analysis by XRD. Alternatively, the first interchangeable optic 125 may be a collimating slit, a one-dimensional mirror or a hybrid monochromator (i.e. parabolic graded multilayer mirror (X-ray mirror) and a channel-cut Ge crystal combined in one module). These optics may be used in various X-ray analysis applications, such as powder diffraction analysis.

The X-ray analysis apparatus 100 may optionally comprise an additional interchangeable optic 127 ("the second interchangeable optic"). The second interchangeable optic 127 may be any of the optics listed in the previous paragraph, as long as it is a different optic to the first interchangeable optic. For example, if the first interchangeable optic 125 is a two-dimensional focusing mirror, the second interchangeable optic may be a monocapillary collimator, a polycapillary collimator, a collimating slit, or a hybrid collimator. The second interchangeable optic 127 may be of the same type as the first interchangeable optic 125, but may have a different structure. For example, both the first interchangeable optic 125 and the second interchangeable optic 127 may be collimating slits, and the two slits may have different dimensions to one another. As illustrated by the circular arrows, the first interchangeable optic 125 can be replaced by (or interchanged with) the second interchangeable optic 127, and vice versa.

The X-ray analysis apparatus 100 also comprises a controller 105. The controller 105 comprises a memory, in which information defining a plurality of X-ray analysis modes is stored. Each X-ray analysis mode may determine the size and/or area of the effective focal spot for that mode, as well as the operating power of the X-ray tube. The different X-ray analysis modes may be optimised for different X-ray analysis applications and/or optics.

In some embodiments, the X-ray analysis mode may be selected based on the type of interchangeable optic to be used for the X-ray analysis application. The controller may store a single X-ray analysis mode corresponding to that optic. That is, the optic may have a one-to-one correspondence with the X-ray analysis mode. Alternatively, the controller may store multiple analysis modes for each optic, and the controller may be configured to select a sub-set of X-ray analysis modes that correspond to the optic.

In FIG. 2, the first interchangeable optic 125 is arranged in the incident X-rays beam path. The controller 105 receives X-ray analysis information, including information identifying the first interchangeable optic 125. The information identifying the first interchangeable optic 125 may be inputted by a user, or it may be received from a sensor (not shown) configured to detect and/or identify the first interchangeable optic 125. The processor 123 processes the information identifying the first interchangeable optic 125 and selects an appropriate X-ray analysis mode. In this way, the controller 105 can select an X-ray analysis mode optimised for the X-ray analysis optic to be used. When there is a one-to-one correspondence between the optic and the X-ray analysis mode, once the appropriate X-ray analysis mode has been selected, the controller communicates with the X-ray analysis apparatus to control the X-ray source to operate according to the selected X-ray analysis mode. When the optic corresponds to multiple X-ray analysis modes, the controller selects the subset of X-ray analysis modes corresponding to the optic. A user may then select from the subset of X-ray analysis modes, and the controller 105 controls the X-ray source 103 to operate according to that mode.

In some embodiments, the controller 105 may be configured to select the X-ray analysis mode based on information other than information identifying the type of optic to be used.

In some embodiments, the controller 105 may be configured to select the X-ray analysis mode based on information relating to the sample. For example, sample size and/or material. Alternatively, the controller may select the X-ray analysis apparatus based on information identifying the type of X-ray analysis application to be conducted.

For example, the X-ray analysis information may comprise information specifying whether the X-ray analysis to be carried out requires high-resolution or low-resolution. Based on that information, the controller may select an appropriate X-ray analysis mode. The controller 105 may be configured to operate the X-ray source 103 in either the first X-ray analysis mode, which is a low-resolution mode, or the second X-ray analysis mode, which is a high-resolution mode. In the high-resolution mode, the aspect ratio of the effective focal spot may be larger than in the low-resolution mode. The controller may determine whether to operate in the high-resolution mode or the low-resolution mode based on information identifying the type of sample, or based on information identifying the type of measurement to be carried out. Note that, in these embodiments, the X-ray analysis apparatus may comprise a single interchangeable optic (i.e. in FIG. 2, it comprises the first interchangeable optic 125 and the second interchangeable optic 127 may not be present), such as a hybrid monochromator.

FIG. 3 illustrates the shape of an effective focal spot in some examples of different X-ray analysis modes.

Figure 3A:
FIG. 3A-3D is a schematic diagram illustrating exemplary effective focal spot shapes of different X-ray analysis apparatus modes.

In FIG. 3A, the effective focal spot is approximately circular. Accordingly, the ratio of the length of the effective focal spot and the width of the effective focal spot (i.e. the aspect ratio of the focal spot) is approximately 1. In some examples, the width and the length of the focal spot may be 20 µm. In those examples, in accordance with the measurement method described herein, the size of the effective focal spot is 20 µm, and the area of the effective focal spot is 400 µm².

Figure 3B:

The effective focal spot of FIG. 3B is similar in shape to that of FIG. 3A, but is larger. In some examples, the largest dimension may be 45 µm, and the aspect ratio may be about 1. Therefore, the size of the effective focal spot is 45 µm and the area of the effective focal spot is 2025 µm².

Figure 3C:

In FIG. 3C the effective focal spot is elongate. In some examples, the length of the focal spot may be about 100 µm and the width of the focal spot may be about 40 µm. Therefore, the size of the effective focal spot is 100 µm.

Figure 3D:

In FIG. 3D the effective focal spot is elongate. In some examples, the length of the focal spot may be about 400 µm and the width of the focal spot may be about 60 µm. Therefore, the size of the effective focal spot is 400 µm. It will be appreciated that these are only examples illustrating the effective focal spots size, and the area of the effective focal spot. The dimensions can be smaller or larger.

Figure 4:
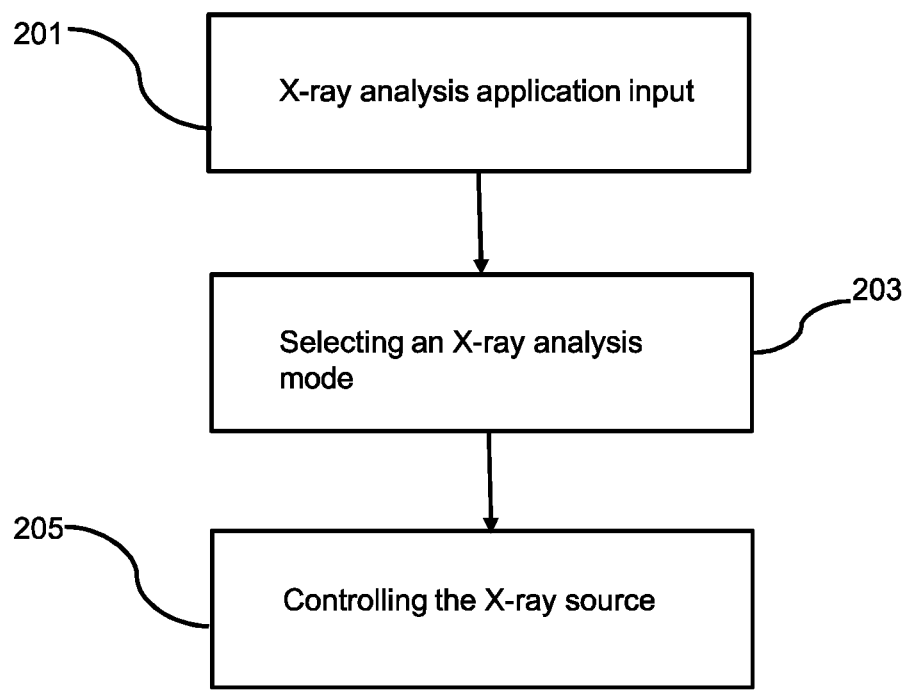
FIG. 4 illustrates a method of X-ray analysis according to an embodiment of the invention.

FIG. 4 illustrates a method of X-ray analysis according to an embodiment of the invention. In an initial step 201, the controller receives X-ray analysis information. The X-ray analysis information may be information identifying an interchangeable optic and/or information relating to the sample to be analysed and/or information identifying the type of X-ray analysis measurement (i.e. the X-ray analysis application) to be carried out. In a subsequent step 203, the controller selects an X-ray analysis mode for the X-ray source based on the received X-ray analysis information. In a further subsequent step 205, the controller communicates with the X-ray source to control the operating voltage and/or filament current of the X-ray tube, thereby controlling the operating power of the X-ray tube. Additionally, the controller communicates with the X-ray source to control the voltage of the focusing arrangement (e.g. the grid voltage) thereby controlling the size of the focal spot.

In some embodiments, the step 201 of inputting X-ray analysis application information may comprise inputting, via a controller, information identifying an interchangeable optic to be used in the X-ray analysis apparatus to carry out the X-ray analysis application. Additionally, the step 203 of selecting the X-ray analysis mode may comprise identifying an X-ray analysis mode that corresponds to the interchangeable optic identified in the previous step. The controller may store a database of X-ray analysis modes. Identifying an X-ray analysis mode that corresponds to the interchangeable optic may comprise identifying multiple X-ray analysis modes, which represent a subset of the X-ray analysis modes in the database. Alternatively, the X-ray analysis mode and the optic may have a one-to-one correspondence, such that identifying an X-ray analysis mode comprises selecting the single X-ray analysis mode corresponding to the identified optic.

In some embodiments, the step 201 of inputting X-ray analysis application information may comprise inputting, via the controller of the X-ray analysis apparatus, information identifying the sample. The step 203 of selecting the X-ray analysis mode may comprise identifying an X-ray analysis mode that corresponds to the sample identified in the previous step. For example, the sample may correspond to a particular optic, and the X-ray analysis apparatus may be capable of interrogating the sample with that optic using both a high-resolution X-ray analysis mode and a low-resolution X-ray analysis mode. A user may select from the high-resolution mode and the low-resolution mode, causing the controller to control the X-ray analysis apparatus to operate according to the selected mode.

In some embodiments, the step 201 of inputting X-ray analysis application information may comprise inputting, via the controller of the X-ray analysis apparatus, information identifying the X-ray analysis application to be carried out. The controller may store a database of X-ray analysis modes. The X-ray analysis application may correspond to one or multiple X-ray analysis modes. The step 203 of selecting the X-ray analysis mode may comprise identifying an X-ray analysis mode that corresponds to the X-ray analysis application identified in the previous step. Identifying an X-ray analysis mode may comprise identifying multiple X-ray analysis modes, which represent a subset of the X-ray analysis modes in the database. Alternatively, the X-ray analysis mode and the optic may have a one-to-one correspondence, such that identifying an X-ray analysis mode comprises selecting the single X-ray analysis mode corresponding to the identified optic.

It will be appreciated that although FIG. 1 shows an X-ray analysis apparatus in which the focusing arrangement comprises grids, alternative focusing arrangements could be used. For example, the focusing arrangement may be a magnetic focusing arrangement, which may provide focusing using magnetic fields. In an example, the focusing arrangement may use a quadrupole magnetic field to achieve focusing.

Further, the focusing arrangement is not necessarily arranged inside the housing or outside of the housing.

When the focusing arrangement does comprise at least one focusing grid, there may be more or fewer than two grids. The X-ray source may comprise a single grid, or multiple grids. Any number of grids may be used.

In general, it will be appreciated that the term "X-ray tube" refers to any X-ray source including a sealed housing in which a cathode and an anode are arranged. The housing may or may not be substantially tubular in shape.

In some embodiments, the cathode may be a coiled wire filament. In some other embodiments, the cathode may comprise a metal loop. The cathode may or may not comprise tungsten.

It will be appreciated that although FIG. 2 shows an X-ray detector for receiving X-rays diffracted and/or scattered by the sample, the X-ray detector could alternatively be an X-ray detector for receiving fluorescence emitted by the sample. In those embodiments, the X-ray detector may be arranged directly above the sample, or in an alternative position.

In some embodiments, the X-ray analysis apparatus may include both an XRF detector and an XRD detector.

The apparatus of FIG. 2 may or may not comprise the second interchangeable optic.

Determining Effective Focal Spot Size and Area

The effective focal spot size is the larger of the length and width of the focal spot, as seen from a measuring device.

The size of the effective focal spot can be determined by an indirect measurement, by measuring geometric unsharpness.

The test method is conducted by imaging sharp edges of a test object. An X-ray image of a highly absorbing test object is obtained, and the size of the effective focal spot is determined using an intensity profile of the image.

Figure 5:
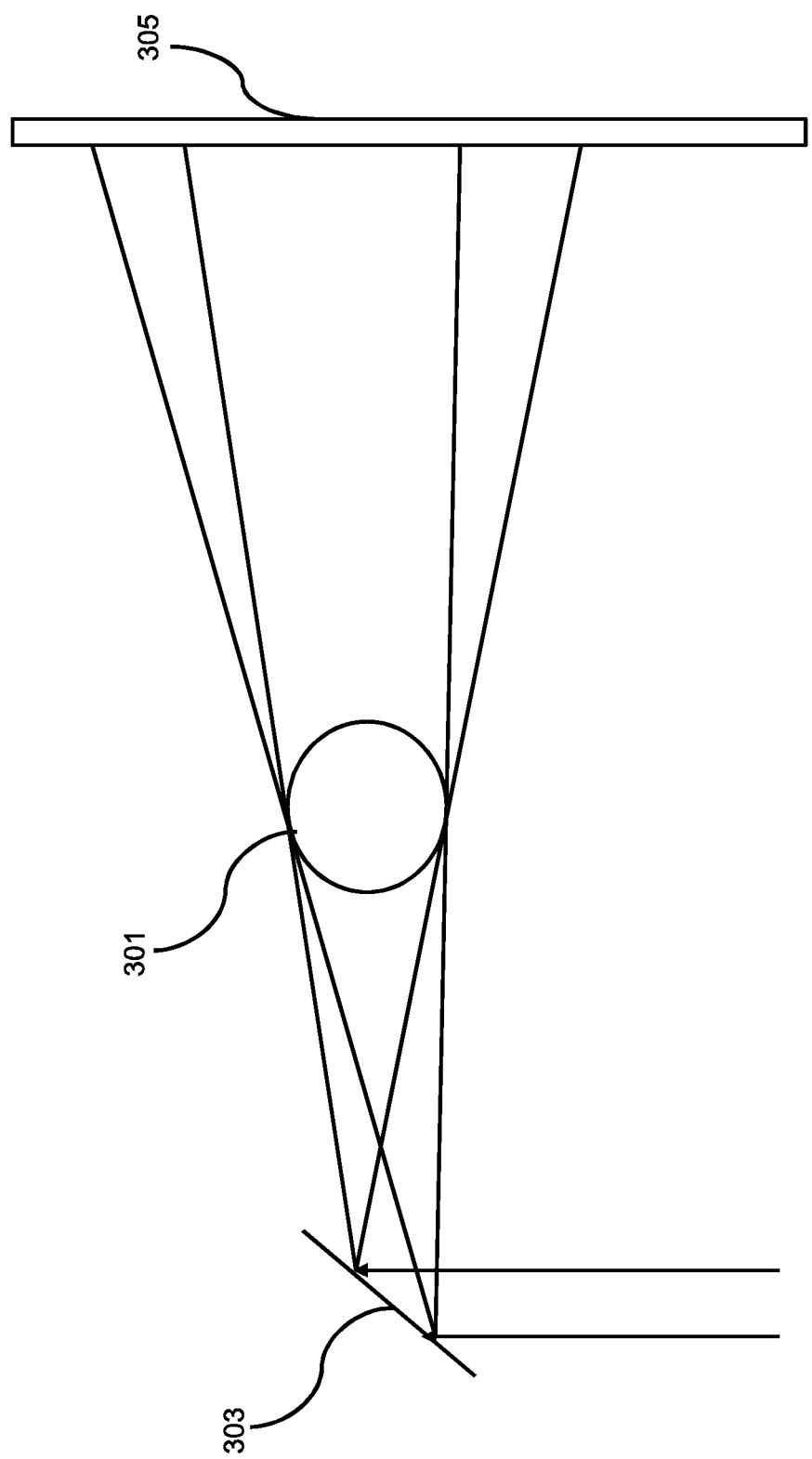
FIG. 5 illustrates an arrangement for measuring the size of the effective focal spot of an X-ray tube.

Referring to FIG. 5, a test object is arranged between the output window of the X-ray tube (not shown) and the detector 305, so as to be irradiated by X-rays emitted from the anode 303. The X-ray tube operating voltage may depend on the operating power of the X-ray tube, and is in any case less than 225 kV. The test object 301 is a spherical ball of tungsten, and has a diameter of 0.9 mm. The ball is mounted on a polyethylene support, at a distance of at least 4.5 cm from the focal spot on the anode. The distance between the test object and the detector 305 enables a projective magnification of between 20× and 100×, wherein the magnification is adjusted to optimise image sharpness (a larger magnification may be required for a relatively small focal spot). The projective magnification is the ratio of the distance from the X-ray tube anode to the detector to the distance from the X-ray tube anode to the test object.

An image of the test object is captured by the detector, and an image processor is used to produce a linear intensity profile in a length direction and a linear intensity profile in a width direction. More specifically, the linear intensity profiles are obtained in the length and width directions along the centre of the image (in the central length direction, and in the central width direction).

The line scan of the image in the central length direction is the intensity profile of the X-ray image, along the centre of the image, in a direction parallel to the longitudinal axis of the X-ray tube. If the longitudinal axis of the X-ray tube is not defined, the central length direction is parallel to the electron trajectory. The width direction is perpendicular to the length direction.

Figure 6:
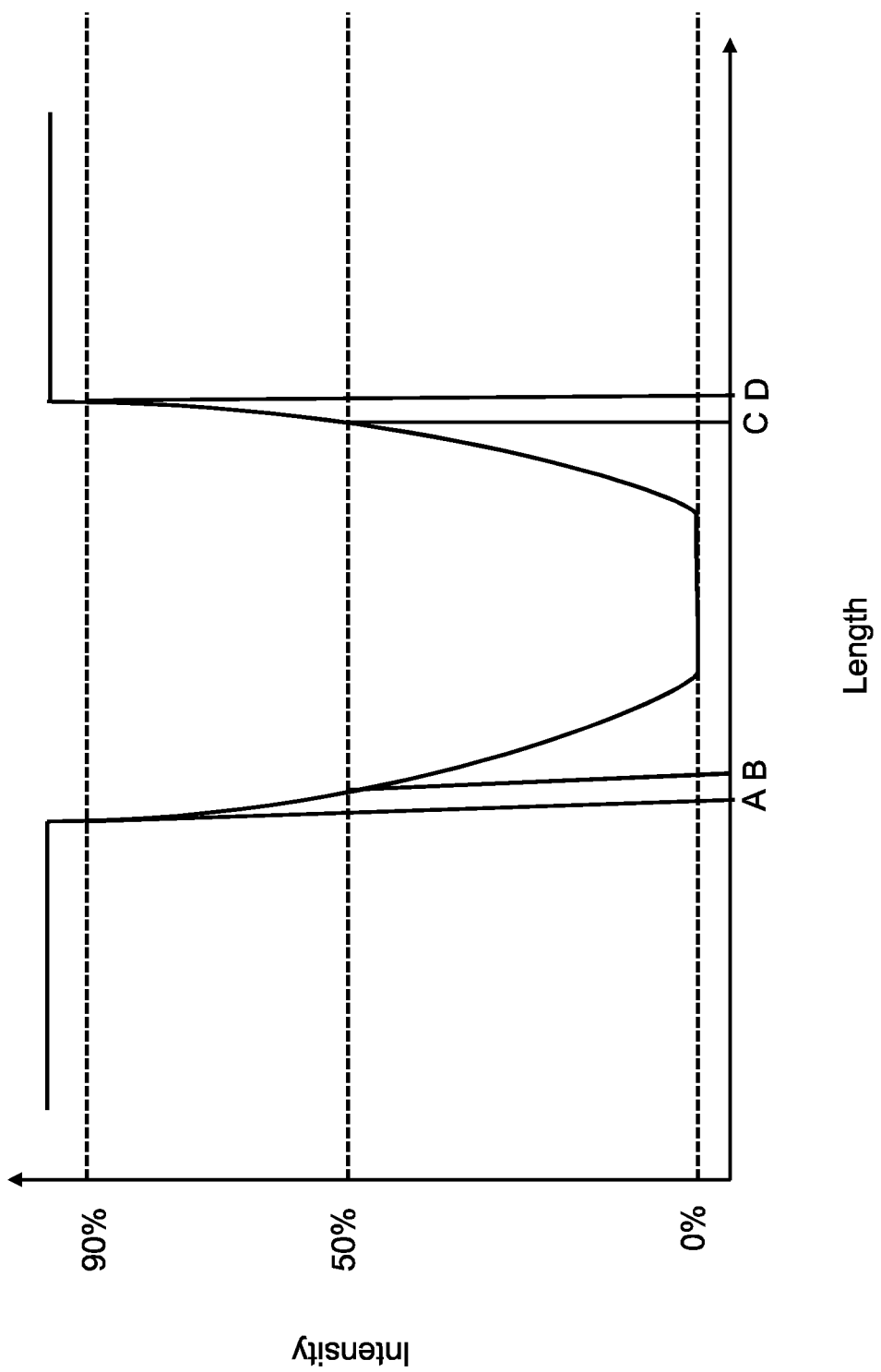
FIG. 6 illustrates a line scan of a test object taken in the length direction, for measuring the length of the effective focal spot.

The image processor then determines the diameter of the test object at 50% of total image contrast by measuring the distance between the two relevant points on the line. For example, in FIG. 6, which shows the line scan in the length direction, the diameter in the length direction ($D_l$) is the distance between points B and C.

Next, two further points (A and D in FIG. 6) are obtained at 90% contrast. The focal spot sizes l and w are then calculated using equations (1) and (2).

$$l = \frac{(\overline{AB} + \overline{CD})}{M_l} \quad (1)$$

$$w = \frac{(\overline{AB} + \overline{CD})}{M_w} \quad (2)$$

$\overline{AB}$ is the distance between points A and B. $\overline{CD}$ is the distance between points C and D. $M_l$ is the geometrical magnification, which is equal to the ratio between the measured diameter ($\overline{BC}$) in the length direction at 50% of the total image contrast and the real diameter (0.9 mm). $M_w$ is the geometrical magnification, which is equal to the ratio between the measured diameter in the width direction at 50% of the total image contrast and the real diameter (0.9 mm).

The skilled person will appreciate that the term "spot" in "focal spot" does not necessarily refer to a round shape, but may instead refer to any two-dimensional shape. As used herein, the area of the effective focal spot is the product of the measured length and the measured width (regardless of the shape of the focal spot).

The invention claimed is:

1. An X-ray analysis apparatus for carrying out a plurality of X-ray analysis applications to analyse a sample by measuring X-ray diffraction and/or X-ray fluorescence, the apparatus comprising:
   an X-ray source for irradiating the sample with X-rays, the X-ray source comprising:
      a solid anode; and
      a cathode for emitting an electron beam;
   a focusing arrangement for focusing the electron beam onto the anode; and
   a controller configured to receive X-ray analysis application information and to control the X-ray analysis apparatus to selectively operate the X-ray source in either a first X-ray analysis mode or a second X-ray analysis mode based on the X-ray analysis application information, wherein:
   in the first X-ray analysis mode the X-ray source is controlled to operate at a first operating power, at a first operating voltage, and has an effective focal spot size that is less than 100 µm; and
   in the second X-ray analysis mode the X-ray source is controlled to operate at a second operating power, at a second operating voltage, wherein the second operating power is greater than the first operating power, and the area of the effective focal spot is greater than the area of the effective focal spot in the first X-ray analysis mode,
   wherein measuring X-ray diffraction comprises receiving X-rays diffracted by the sample, or wherein measuring X-ray fluorescence comprises receiving fluorescence emitted by the sample.

2. The X-ray analysis apparatus of claim 1, wherein in the first X-ray analysis mode the X-ray source has an effective focal spot size less than 55 µm and in the second X-ray analysis mode the effective focal spot size is greater than 60 µm.

3. The X-ray analysis apparatus of claim 1, further comprising a first interchangeable X-ray optic arranged to receive X-rays from the X-ray source.

4. The X-ray analysis apparatus of claim 3, wherein the controller is configured to receive information identifying the first interchangeable X-ray optic, and wherein the controller is configured to operate the X-ray analysis apparatus in either the first X-ray analysis mode or the second X-ray analysis mode based on the information identifying the first interchangeable X-ray optic.

5. The X-ray analysis apparatus of claim 1, wherein the effective focal spot has an aspect ratio greater than 2.0 in both the first X-ray analysis mode and the second X-ray analysis mode, and the controller is configured to receive sample information and to operate the X-ray analysis apparatus in the first X-ray analysis mode or the second X-ray analysis mode based on the sample information.

6. The X-ray analysis apparatus according to claim 1, wherein in the first X-ray analysis mode the effective focal spot size is less than 40 µm, the aspect ratio of the effective focal spot is less than 1.5 and the first operating power is less than 50 W.

7. The X-ray analysis apparatus according to claim 1, wherein in the second X-ray analysis mode, the effective focal spot size is greater than in the first X-ray analysis mode and greater than 60 µm, the aspect ratio of the effective focal spot is less than 1.5, and the second operating power is greater than 50 W.

8. The X-ray analysis apparatus according to claim 1, wherein in the first X-ray analysis mode, the effective focal spot has an aspect ratio that is less than 1.5, and in the second X-ray analysis mode the focal spot is elongate and has an aspect ratio that is greater than 2.0.

9. The X-ray analysis apparatus according to claim 8, wherein in the second X-ray analysis mode the effective focal spot size is greater than 60 µm and the second operating power is greater than 50 W.

10. The X-ray analysis apparatus according to claim 1, wherein the effective focal spot size in the second X-ray analysis mode is greater than 100 µm, and the second operating power is equal to or greater than 100 W.

11. The X-ray analysis apparatus according to claim 1, further comprising:
   a sample stage for supporting the sample, wherein the sample stage is arranged such that the X-ray source irradiates the sample with X-rays directed along an incident beam path; and
   a detector arranged to receive X-rays scattered by the sample or emitted from the sample.

12. The X-ray analysis apparatus of claim 11, wherein the X-ray analysis apparatus comprises a first interchangeable X-ray optic, and wherein the X-ray analysis apparatus further comprises:
   a first actuator configured to move the first interchangeable X-ray optic between an in-beam position, in which the first interchangeable X-ray optic is arranged in the incident beam path, and an out-of-beam position, in which the first interchangeable X-ray optic is arranged outside of the incident beam path;
   wherein the controller is configured to receive information identifying the position of the first interchangeable X-ray optic and to operate the X-ray analysis apparatus in the first X-ray analysis mode or the second X-ray analysis mode based on the position of the first interchangeable X-ray optic.

13. A method of controlling the X-ray analysis apparatus of claim 1 comprising:
- receiving, by a controller, X-ray analysis application information;
- selecting a first X-ray analysis mode or a second X-ray analysis mode based on the X-ray analysis application information; and
- controlling the X-ray source to operate in the selected mode, wherein:
- in the first X-ray analysis mode the X-ray source is controlled to operate at a first operating power, and has an effective focal spot size that is less than 100 µm; and
- in the second X-ray analysis mode the X-ray source is controlled to operate at a second operating power, which is higher than the first operating power, and the area of the effective focal spot is greater than the area of the effective focal spot in the first X-ray analysis mode.

14. The method of claim 13, wherein in the first X-ray analysis mode the X-ray source has an effective focal spot size less than 55 µm and in the second X-ray analysis mode the effective focal spot size is greater than 60 µm.

15. A computer program product comprising a tangible non-transitory computer readable medium in which program instructions are stored, wherein the program instructions cause an X-ray analysis apparatus to execute the steps of the method of claim 13.

* * * * *